United States Patent
Tao et al.

(10) Patent No.: US 9,127,022 B2
(45) Date of Patent: Sep. 8, 2015

(54) METHOD FOR PREPARING SURFACE-MODIFIED NANOSILICON DIOXIDE FROM RICE HULLS

(71) Applicant: Wuhan Kaidi Engineering Technology Research Institute Co., Ltd., Wuhan (CN)

(72) Inventors: Leiming Tao, Wuhan (CN); Yilong Chen, Wuhan (CN); Yanfeng Zhang, Wuhan (CN); Yongjie Xue, Wuhan (CN)

(73) Assignee: Wuhan Kaidi Engineering Technology Research Institute Co., Ltd., Wuhan (CN)

( * ) Notice: Subject to any disclaimer, the term of this patent is extended or adjusted under 35 U.S.C. 154(b) by 0 days.

(21) Appl. No.: 14/569,771

(22) Filed: Dec. 14, 2014

(65) Prior Publication Data

US 2015/0119595 A1    Apr. 30, 2015

Related U.S. Application Data

(63) Continuation-in-part of application No. PCT/CN2013/076864, filed on Jun. 6, 2013.

(30) Foreign Application Priority Data

Jun. 15, 2012 (CN) .......................... 2012 1 0196923

(51) Int. Cl.
*C01B 33/023* (2006.01)
*C07F 7/02* (2006.01)

(52) U.S. Cl.
CPC ...................................... *C07F 7/025* (2013.01)

(58) Field of Classification Search
USPC .................................. 556/400; 423/335, 337
See application file for complete search history.

(56) References Cited

U.S. PATENT DOCUMENTS 8,178,067 B2 * 5/2012 Kondoh et al. ............... 423/335

* cited by examiner

*Primary Examiner* — Sudhakar Katakam
*Assistant Examiner* — Pancham Bakshi
(74) *Attorney, Agent, or Firm* — Matthias Scholl P.C.; Matthias Scholl

(57) ABSTRACT

A method for preparing surface-modified nano silicon dioxide from rice hulls. The method includes: 1) pretreating rice hulls using a treating gas containing $CO_2$ to remove metal ions, impurities, and dusts, and desiccating and grinding the rice hulls; 2) submerging the rice hulls into a dilute solution of phosphoric acid, boric acid, hydrochloric acid, formic acid, acetic acid, propionic acid, butyric acid, or a strong-acid-weak-base salt for between 4 and 8 hrs, controlling the immersion temperature not to exceed 10° C., leaching a resulting mixture, removing a filtrate, and desiccating the rice hulls; and 3) calcining the rice hulls in the absence of oxygen at a temperature of between 300 and 450° C.

12 Claims, 5 Drawing Sheets

METHOD FOR PREPARING SURFACE-MODIFIED NANOSILICON DIOXIDE FROM RICE HULLS

CROSS-REFERENCE TO RELATED APPLICATIONS

This application is a continuation-in-part of International Patent Application No. PCT/CN2013/076864 with an international filing date of Jun. 6, 2013, designating the United States, now pending, and further claims priority benefits to Chinese Patent Application No. 201210196923.X filed Jun. 15, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

1. Field of the Invention

The invention relates to the field of preparation of surface-modified nano silicon dioxide materials from rice hulls.

2. Description of the Related Art

Conventional methods for producing nano silicon dioxide mainly include a precipitation method and a gas phase method. Primary raw materials used in such methods are from non-renewable resources, such as quartz and wollastonite, and the production process of the raw materials consumes large energy, causes serious pollution, and requires complex post-processing procedures. In addition, nano silicon dioxide prepared by such methods is usually hydrophilic, which cannot meet the current industrial requirements, so that it is necessary to conduct surface modification. At present, the modification method mainly utilizes appropriate chemical substance to react with hydroxyl radicals on the surface of the nano silicon dioxide to remove or decrease the amount of silanol groups on the surface and to transform the products from hydrophilicity into hydrophobicity. However, the modification method consumes a large amount of chemicals and involves complex processes, which increases the production costs.

SUMMARY OF THE INVENTION

In view of the above-described problems, it is one objective of the invention to provide a method for preparing surface-modified nano silicon dioxide from rice hulls. The surface-modified nano silicon dioxide prepared by the method is hydrophobic amorphous nano silicon dioxide having a grain size of between 60 and 200 nm.

To achieve the above objective, in accordance with one embodiment of the invention, there is provided a method for preparing surface-modified nano silicon dioxide from rice hulls, the method comprising:

1) pretreating rice hulls using a treating gas containing $CO_2$ to remove metal ions, impurities, and dusts, and desiccating and grinding the rice hulls;
2) submerging the rice hulls into a dilute solution of phosphoric acid, boric acid, hydrochloric acid, formic acid, acetic acid, propionic acid, butyric acid, or a strong-acid-weak-base salt for between 4 and 8 hrs, controlling an immersion temperature not to exceed 10° C., leaching a resulting mixture, removing a filtrate, and desiccating the rice hulls; and
3) calcining the rice hulls in the absence of oxygen at a temperature of between 300 and 450° C., whereby obtaining a surface-modified nano silicon dioxide.

In a class of this embodiment, the treating gas containing $CO_2$ in step 1) is industrial flue gas.

In a class of this embodiment, pretreating of the rice hulls using the treating gas containing $CO_2$ in step 1) comprises: providing a water storage reactor, disposing a gas dispersion device at a bottom of the water storage reactor, and filling the water storage reactor with water; bagging the rice hulls and placing them in the water storage reactor, and submerging them in the water; allowing industrial flue gas to be bubbled into the water via the gas dispersion device to increase a solubility of carbon dioxide of the industrial flue gas in the water to produce a carbonic acid solution; allowing the carbonic acid solution to react with the metal ions of the rice hulls to produce a precipitant; and washing the rice hulls after the reaction, and using deionized water to wash and squeeze the rice hulls to remove attached metal ions from the rice hulls.

In a class of this embodiment, the solubility of carbon dioxide in the system of the water storage reactor in the pretreating process by using the treating gas containing $CO_2$ reaches 1 g of carbon dioxide dissolved in 100 g of water.

In a class of this embodiment, a treating time for the pretreating using the treating gas containing $CO_2$ is between 1 and 6 days.

In a class of this embodiment, the water storage reactor has a depth of between 6 and 10 m. The water storage reactor should possess an appropriate depth so as to dissolve the carbon dioxide of the industrial flue gas ejected from the bottom of the pool in the water and to produce a carbonic acid solution having a proper concentration.

The gas dispersion apparatus is provided with gas getting holes configured to horizontally or vertically agitate water to form vortexes; and the industrial flue gas is ejected from the gas getting holes. During the vortex agitation of the water, a degree of dispersion of carbon dioxide in the water is further enlarged, thereby increasing a concentration of carbonic acid.

In a class of this embodiment, the gas dispersion apparatus comprises a longitudinal gas pipe and at least one annular gas pipe horizontally arranged and communicating with an upper end of the longitudinal gas pipe. A plurality of gas getting holes is circumferentially disposed on the annular gas pipe and faces inclinedly downwards so that the ejected flue gas enables the water to produce a vortex agitation.

In a class of this embodiment, an angle between an axis of each gas getting hole and a horizontal plane is between 5 and 35°, and preferably 20°.

In a class of this embodiment, a distance between a height of the annular gas pipe and a bottom of the water storage reactor exceeds 1.5 m. Because the precipitant is produced in the reaction between carbonic acid and the rice hulls, the arrangement of the annular gas pipe should satisfy the distance between the annular gas pipe and the bottom of the water storage reactor of more than 1.5 m in order to prevent the precipitant from obstructing the gas getting holes.

In a class of this embodiment, a plurality of gas jetting mouths is disposed on a pipe wall of the longitudinal gas pipe and faces inclinedly upwards. The arrangement of the gas jetting mouths on the longitudinal gas pipe is utilized to achieve the vortex agitation of the water by the ejected gas from the gas jetting mouths, so that the water of the upper layer and the lower layer can be circulated, the dissolved gas is uniformly distributed, and the solubility of the gas in the water is further increased.

In a class of this embodiment, an angle between an axis of each gas jetting mouth and a vertical direction is between 10 and 45°, and preferably 20°.

In a class of this embodiment, the longitudinal gas pipe is disposed at a center of the annular gas pipe and communicates with the annular gas pipe via a transvers gas pipe.

In a class of this embodiment, the annular gas pipe comprises: an upper layer annular gas pipe, a middle layer annular gas pipe, and a lower layer annular gas pipe. The upper layer annular gas pipe, the middle layer annular gas pipe, and the lower layer annular gas pipe have sequentially increased diameters and are arranged on the longitudinal gas pipe from top to bottom to form a tower configuration. The annular gas pipes of the tower configuration are capable of eliminating dead angle for the industrial flue gas to disperse into the water, forming vortex agitation in the water, and preventing the dust in the water from obstructing the gas jetting holes.

In a class of this embodiment, each gas jetting hole or gas jetting mouth of the gas dispersion apparatus is provided with a plurality of microporous aerators.

In a class of this embodiment, a pore diameter of the gas jetting hole is between 0.005 and 0.012 mm, and a pore diameter of the gas jetting mouth is between 4 and 6 mm. Gas ejected from the gas jetting hole satisfies Laplace formula, that is, when an additional pressure of a spherical liquid surface is directly proportional to a surface tension coefficient and is inversely proportional to a spherical radius; in conditions of a certain surface tension coefficient, the smaller the radius is, the larger the additional pressure is. The smaller the pore diameter is, the smaller the ejected bubble is. When the small bubble of carbon dioxide is jetted from a jet nozzle, the bubble enlarges while the surface tension quickly decreases, and the bubble then busts. Thus, a contact area between the carbon dioxide and the water enlarges, and the forming speed of carbonic acid in the water increases. By changing the depth of the gas jetting holes arranged in the water and the pore diameter of the gas jetting holes, the amount of the carbon dioxide dissolved in the water is regulated, thereby further regulating the concentration of carbonic acid.

In a class of this embodiment, the pretreating of the rice hulls using the treating gas containing $CO_2$ in step 1) comprises: arranging a gas distributor provided with microporous aerators in a lower part of a reaction tank; arranging a circulating fluid outlet on a wall of the reaction tank beneath the gas distributor, arranging a gas outlet at a top of the reaction tank, arranging a precipitant outlet at a bottom part of the reaction tank, and arranging a movable grid-like package pressing plate in the upper part of the reaction tank; in use of the reaction tank, filling the reaction tank with rice hulls and water, pressing the rice hulls below a water surface using the grid-like package pressing plate, fixing the grid-like package pressing plate, and controlling the gas outlet at a close state; ejecting the industrial flue gas from the microporous aerator of the gas distributor, utilizing a pressure of the industrial flue gas in the reaction tank to increase a solubility of carbon dioxide of the industrial flue gas in the water and to produce a carbonic acid solution, and allowing the carbonic acid solution to react with metal ions of the rice hulls to produce a precipitant; and washing the rice hulls after the reaction, and using desalinated water to wash and squeeze the rice hulls to remove attached metal ions from the rice hulls.

In a class of this embodiment, a mist eliminator is disposed above the grid-like package pressing plate.

In a class of this embodiment, the solubility of carbon dioxide in the system of the water storage reactor in the pretreating using the treating gas containing $CO_2$ reaches 4 g of carbon dioxide dissolved in 100 g of water.

In a class of this embodiment, an immersion temperature in step 2) is preferably between −5 and 5° C.; and a ratio of a weight of the rice hulls to a volume of the dilute solution for immersion is 1: 5-20 g/mL.

In a class of this embodiment, step 2) further comprises washing and grinding before desiccating.

In a class of this embodiment, a heating rate of step 3) is between 8 and 20° C./min; and a time for calcination in the absence of oxygen is between 1 and 3 h.

Principle of the method for preparing surface-modified nano silicon dioxide from rice hulls in the above scheme is as follows: carbon dioxide of the industrial flue gas is dissolved in the water to produce carbonic acid so as to acidify the rice hulls and to react with metal ions such as aluminum, calcium, magnesium, iron, and manganese to produce insoluble salts. The precipitant formed in the reaction are primarily metal carbonates or oxides, so that the metal ions on the rice hulls are effectively removed. Although carbon dioxide ($CO_2$) is nonpolar molecule, it can still be dissolved into solvent of strong polar nature. The solubility relates to the temperature, the pressure, and the nature of the solvent. In conditions of normal temperature and normal pressure, a volume ratio of carbon dioxide to water in a saturated aqueous solution is approximately 1: 1, a majority of carbon dioxide exists in the form of combining with relatively weak hydrate molecules, and only a small amount thereof form carbonic acid the concentration of which, however, cannot process a large quantities of rice hulls. In conditions of the pressure of carbon dioxide smaller than 0.5 MPa, the solubility thereof is directly proportional to the pressure thereof; and in conditions the pressure of carbon dioxide exceeding 0.5 MPa, because of the formation of the carbonic acid, the increase amplitude of the solubility of carbon dioxide will increase along with the increase of the pressure. thus, to increase the concentration of carbonic acid in the water to satisfy the requirement of removing metal ions of the rice hulls, it is critical to improve the pressure of carbon dioxide.

Three means are utilized to increase an equilibrium pressure of carbon dioxide on the liquid surface: a first means is utilizing the water pressure, a second means is selecting some gas dispersion apparatus, and a third means is selecting closed containers to increase gas pressure on the liquid surface inside the container. The method adopting the water storage reactor provided by the invention is that utilizing the water pressure and the gas dispersion apparatus to improve the solubility of carbon dioxide in the water, while the method adopting the reaction tank is utilizing the closed container to achieve a high pressure of carbon dioxide on the liquid surface inside the container and to accelerate the dissolving of carbon dioxide, thereby realizing good removal effect of metal ions.

Rice hulls are a type of an organic-inorganic composite material, and amorphous silicon dioxide and lignin are tightly combined by hydroxy covalent bonds and are mainly distributed in a lignin layer of the rice hulls. The lignin contains a large amount of phenolic compounds which are composed of phenols or polyphenols and difficult to decompose in weak acid condition. Hydroxyl radicals in cellulose and semicellulose are straight-chain hydroxyls, different structures result in difference in degree of difficulty for decomposition. By controlling the concentration of the acid, the immersion temperature, and the immersion time, the cellulose is decomposed into short chains of xyloses while the polyphenols in the lignin cannot be decomposed. Thus, the decomposition of the lignin is prevented, and the decomposition of the cellulose and the semicellulose into small molecule xyloses is ensured. Thereafter, the hulls rice is calcined at the temperature of between 300 and 450° C. by controlling the calcination condition. Because the amorphous silicon dioxide is prone to bind with hydroxyls, the organic compound containing hydroxyl is bonded on the surface of the amorphous silicon dioxide, and therefore the surface of the amorphous silicon dioxide is wrapped with a layer of the organic compound. That is, hydrophilic hydroxyl groups are surrounded by hydrophobic benzene rings to form the hydrophobic silicon dioxide, which is the same as using the modifier to modify the surface of silicon dioxide, thereby achieving the surface modification of silicon dioxide. In conditions of a too low calcining temperature (below 300° C.), it is difficult to active bond break in silicon dioxide thereby preventing the formation of particles of grain size; and in conditions of a too high calcining temperature (exceeding 450° C.), silicon dioxide is easily recrystallized and agglomerated into large particles and polyphenols are obviously decomposed. The anaerobic condition is capable of preventing organic compounds on the surface of the silicon dioxide from combustion at the high temperature.

The rice hulls of the agriculture byproducts are pretreated by the industrial flue gas containing $CO_2$ for removing metal ions, impurities, and dust, acid leached using the diluted acid solution for further decomposing cellulose and semicellulose, calcined at the temperature of between 350 and 450° C. in the absence of oxygen to break bonds of silicon dioxide, and wrapped with a layer of the organic compound, that is, the hydrophilic hydroxyl groups are surrounded by hydrophobic benzene rings to form the hydrophobic silicon dioxide, which is the same as using the modifier to modify the surface of silicon dioxide, thereby achieving the surface modification of silicon dioxide.

Advantages according to embodiments of the invention are as follows:

The method of the invention utilizes structure features of the rice hulls and is adapted to directly prepare the surface-modified nano silicon dioxide without adding any modifiers. The process is simply controlled, low-carbon and environment protective, and has high comprehensive benefits. The prepared surface-modified nano silicon dioxide is amorphous nano silicon dioxide having a grain size of between 60 and 200 nm, a liphophilic value of between 1.00 and 2.50 mL/g, a water surface contact angle of >128°, and a BET specific surface area of between 60 and 120 $m^2/g$.

Carbon dioxide preferably adopts the industrial flue gas (comprising power plant flue gas or industrial exhaust gas) containing a large amount of carbon dioxide to conduct removal of metal ions from the rice hulls, which not only saves the production cost, but also utilizes the industrial flue gas and prevents the environment pollution of the waste gas. In addition, the solution after treating the rice hulls contains soluble matters of nutrient elements necessitated by plants such as sodium, potassium, nitrogen, phosphorus, and sulfur, and can be directly used as a nutrient solution for plants. Precipitants produced in the reaction can be used in constructions or as material additives, thereby avoiding water pollution.

Figure 1:
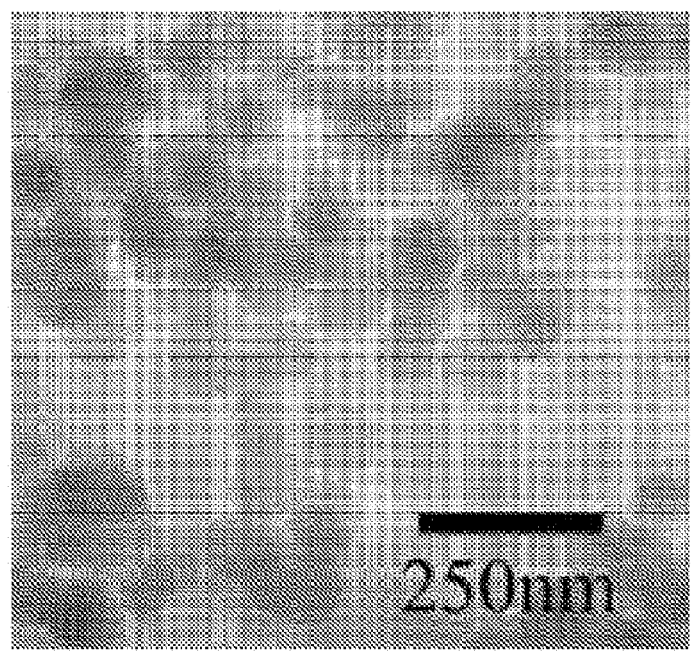
FIG. 1 is a transmission electron microscope picture of a surface-modified silicon dioxide prepared according to Example 1.

In the drawings, the following reference numbers are used: 1. Water storage reactor; 2. Longitudinal gas pipe; 3. Annular gas pipe; 3.1. Upper layer annular gas pipe; 3.2. Middle layer annular gas pipe; 3.3. Lower layer annular gas pipe; 4. Gas main; 5. Rice hulls; 6. Transverse gas pipe; 7. Package pressing strip; 8. Circulating liquid outlet; 9. Gas distributor; 10. Precipitant outlet; 11. Tapered part; 12. Gas outlet; 13. Grid-like package pressing plate; 14. Mist eliminator; and 15. Reaction tank.

DETAILED DESCRIPTION OF THE EMBODIMENTS

For a better understanding the invention, the context of the invention is further illustrated combined with embodiments. However, the context of the invention is not limited to the following embodiment, and the embodiments should not be considered as restrictions of the invention.

EXAMPLE 1

Figure 5:
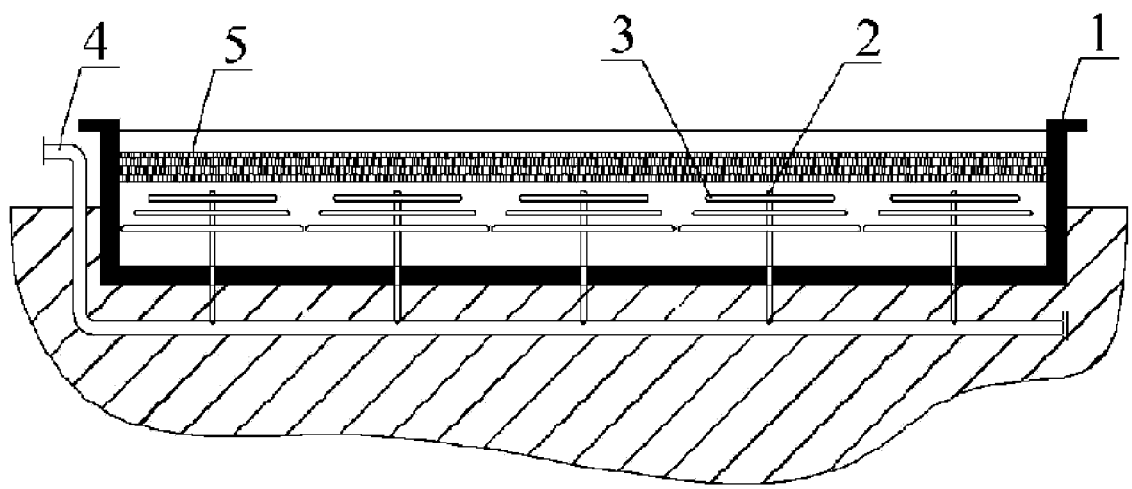
FIG. 5 is a cross sectional view of a water storage reactor according to Example 1.
Figure 6:
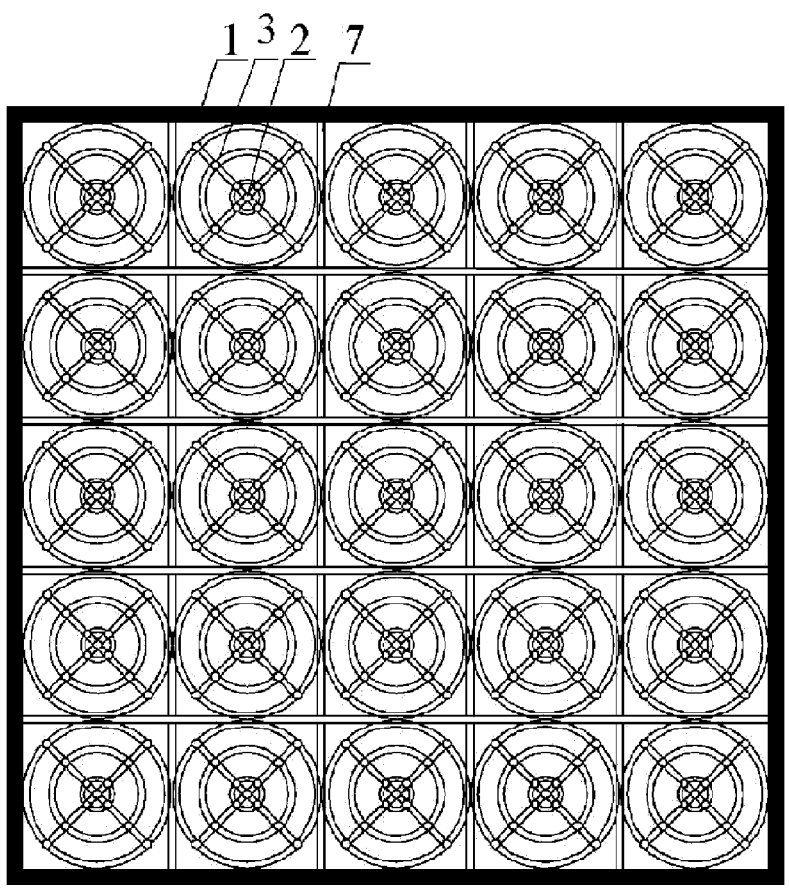
FIG. 6 is a top view of a FIG. 5.

1. 10 kg of rice hulls are collected and treated by industrial flue gas in order to remove metal ions, impurities, and dusts, which is specifically conducted as follows:

(1) As shown in FIGS. 5-6, a water storage reactor 1 having a depth of 7 m and both a width and a length of 100 m is constructed. 25 gas dispersion apparatus for discharging industrial flue gas are disposed at a bottom part of the water storage reactor. Each gas dispersion apparatus comprises a longitudinal gas pipe 2 and at least one annular gas pipe 3 being horizontally arranged and communicating with an upper end of the longitudinal gas pipe.

Specifically, a plurality of gas jetting holes (not shown in the drawings) is circumferentially disposed on the annular gas pipe and faces inclinedly downwards, so that a vortex agitation of the water body is produced by the ejected flue gas. An angle between an axis of the gas jetting hole and a horizontal plane is 20°. A projection of the axis of the gas jetting mouth on the horizontal plane is tangent to an annular edge of the annular gas pipe 3, and the gas jetting holes are disposed on the annular gas pipe 3 in a clockwise direction or a counter clockwise direction.

Specifically, a plurality of gas jetting mouths (not shown in the drawings) is disposed on a pipe wall of the longitudinal gas pipe 2 and faces inclinedly upwards. An angle between an axis of each gas jetting mouth and a vertical direction is 20°.

Specifically, the gas jetting hole or gas jetting mouth of the gas dispersion apparatus is provided with a plurality of microporous aerators, and the industrial flue gas is ejected out of the microporous aerators.

Specifically, a distance between a height of the annular gas pipe 3 and the bottom of the pool is 1.5 m.

Figure 7:
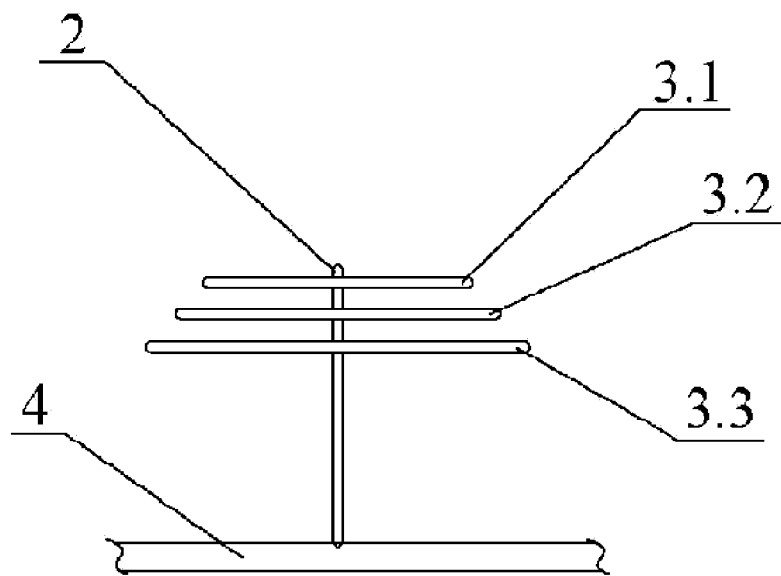
FIG. 7 is an enlarged structure diagram of annular gas pipes and a longitudinal gas pipe in FIG. 5.
Figure 8:
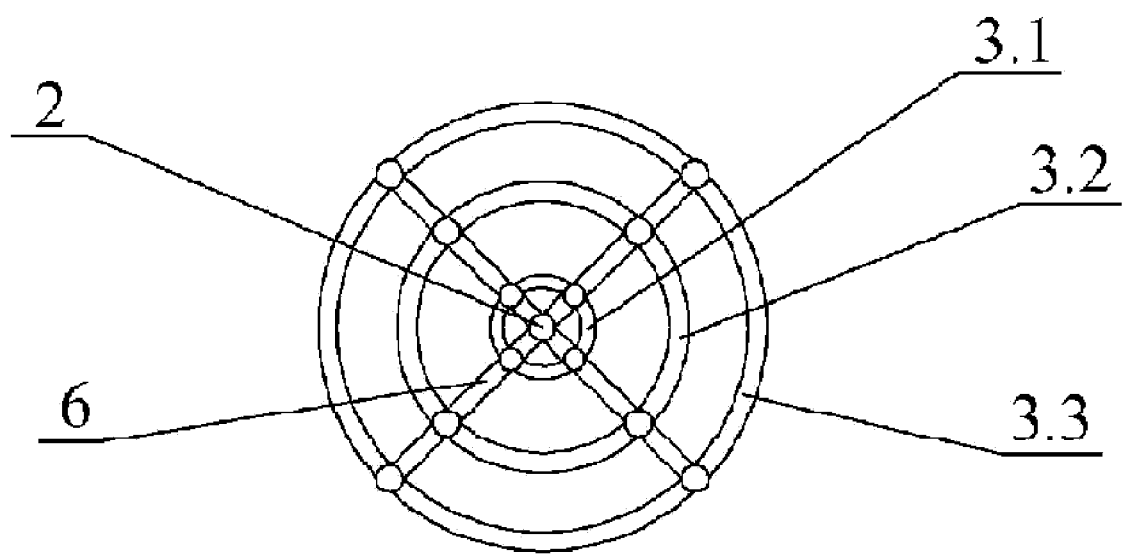
FIG. 8 is a top view of FIG. 7.
Figure 9:
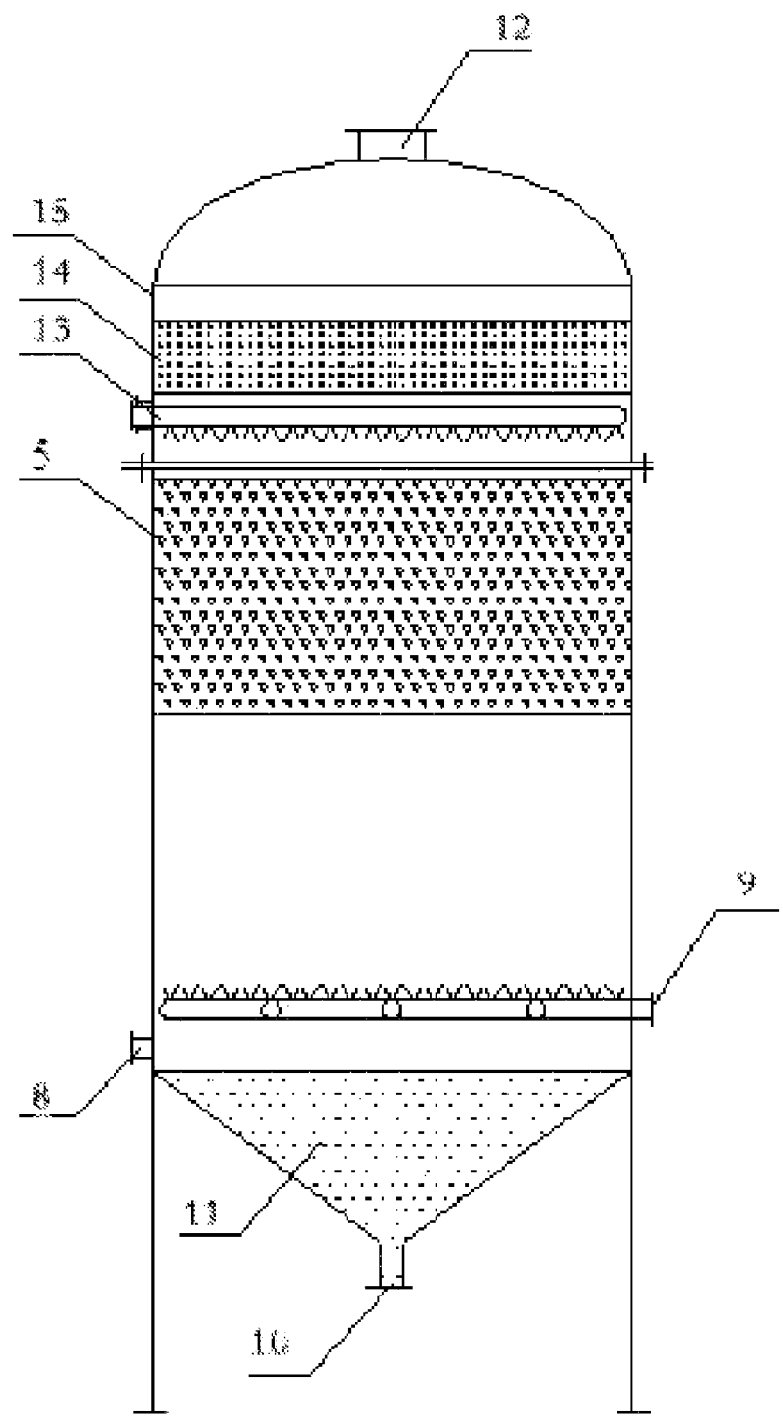
FIG. 9 is a cross sectional view of a reaction tank according to Example 2.

As shown in FIGS. 7-8, the annular gas pipe 3 comprises: an upper layer annular gas pipe 3.1, a middle layer annular gas pipe 3.2, and a lower layer annular gas pipe 3.3. The upper layer annular gas pipe 3.1, the middle layer annular gas pipe 3.2, and the lower layer annular gas pipe 3.3 have sequentially increased diameters and are arranged on the longitudinal gas pipe 2 from top to bottom to form a tower configuration.

As shown in FIG. 8, the longitudinal gas pipe 2 is disposed at a center of the annular gas pipe 3 and communicates with the annular gas pipe 3 via a transvers gas pipe 6.

A bore diameter of the gas jetting hole is 0.01 mm, and a bore diameter of the gas jetting mouth is between 4 and 6 mm.

(2) The rice hulls 5 is packed and the rice hulls packages are threw into the water storage reactor 1, and then a package pressing strip 7 is used to press the rice hulls packages downward below a water surface.

(3) The industrial flue gas containing carbon dioxide discharged from biomass power plant is treated by dust collecting equipment for removing dust therefrom, introduced to a gas main 4, and ejected into the water storage reactor containing water having a depth of 5.5 m by the gas dispersion apparatus 2. Under the action of the pressure, an amount of carbon dioxide of the industrial flue gas dissolved in water is increased to 5 times of that in conditions of normal temperature and normal pressure, and the solubility is 100 g of water dissolving 1 g of carbon dioxide. Carbonic acid solution produced acidifies the rice hulls 5 and reacts with metal ions to produce a precipitant. After the reaction, the rice hulls 5 are washed and deionized water is used to wash and squeeze the rice hulls so as to remove the attached metal ions from the rice hulls 5.

In the process of rice hulls treatment, soluble matters and precipitants are produced. The soluble matters are abundant in nitrogen, phosphorus, potassium, sodium, and small organic molecules. The precipitants are primarily metal carbonates or oxides containing aluminum, calcium, magnesium, iron, and manganese. Reaction insoluble matters and the dust in the flue gas are precipitated in the bottom of the water storage reactor to form a sediment layer. A cycle for the treatment of the rice hulls using the water storage reactor is 6 days. After being washed twice, the rice hulls is further washed and squeezed by deionized water, so that between 60% and 70% of metal ions of the rice hulls are removed. The water storage reactor is capable of treating 2500 tons rice hulls once.

2. The rice hulls pretreated by the above step are dried, and grinded. 1 kg of the grinded hulls are collected and added to 5 L of a boric acid solution having a molar concentration of 0.1 M. A resulting mixture is placed in an ice bath at a temperature of 0° C. for 8 hrs. After that, a filtration device is utilized to filtrate surplus solution and the boric acid solution and to obtain a composite containing an organic matter and silicon. The composite containing the organic matter and silicon is then dried at a temperature of 110° C.

3. The composite containing the organic matter and silicon is placed in a tube furnace in the presence of nitrogen and heated to a temperature to 400° C. at a heating rate of 10° C./min, after heat preservation for 1 h, silicon dioxide powder is obtained. The silicon dioxide powder is tested by a transmission electron microscope, X-ray diffraction (XRD), an energy dispersive spectrometer, and infrared test, and corresponding test results are shown in FIGS. 1-4.

As shown in FIG. 1, silicon dioxide in the silicon dioxide powder is round particle, evenly dispersed, and has a grain size of 120 nm.

Figure 2:
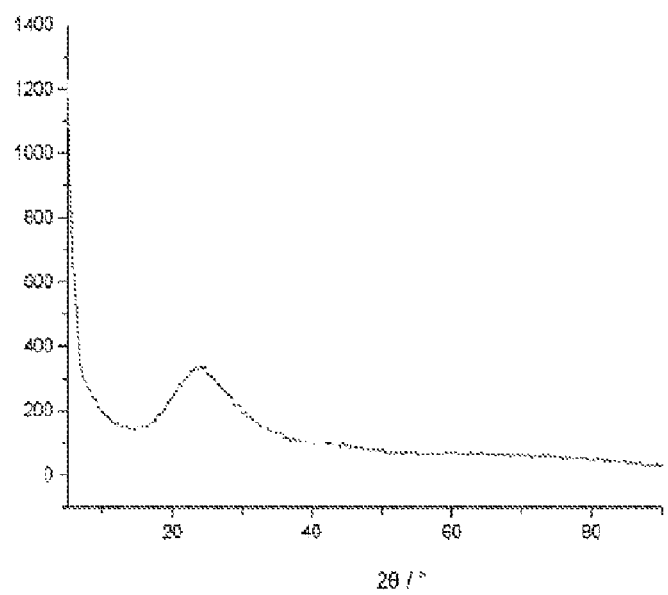
FIG. 2 is an XRD chart of a surface-modified silicon dioxide prepared according to Example 1.

As shown in FIG. 2, the silicon dioxide powder is amorphous silicon dioxide.

Figure 3:
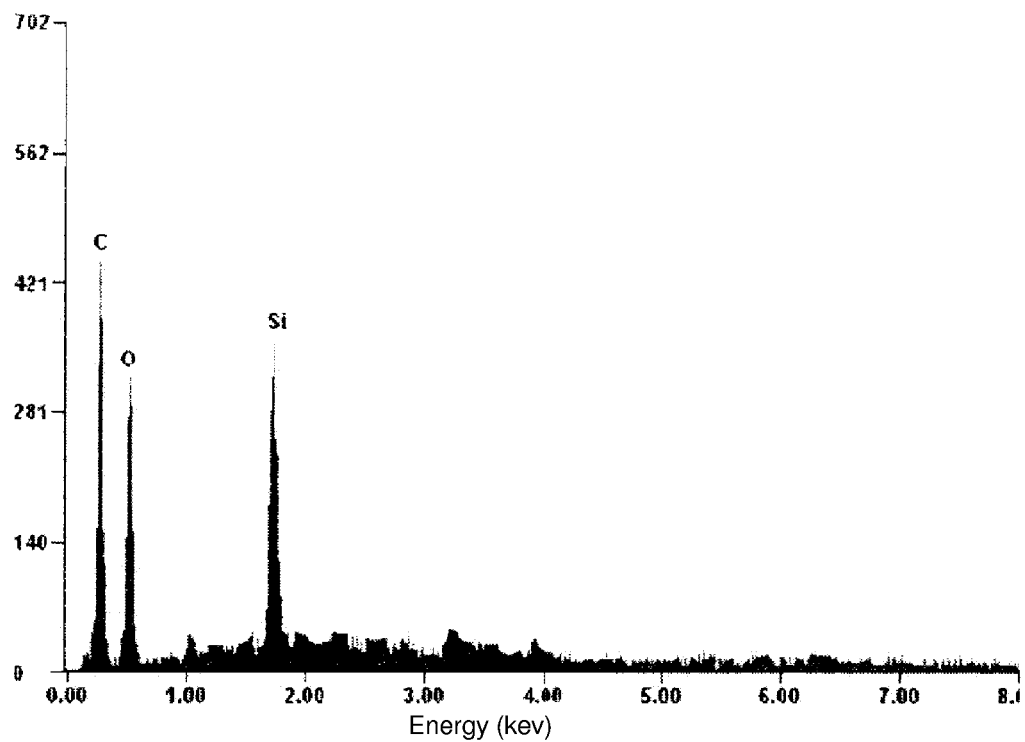
FIG. 3 is an energy spectrum of a surface-modified silicon dioxide prepared according to Example 1.

As shown in FIG. 3, the silicon dioxide powder contains silicon dioxide and organic compound.

Figure 4:
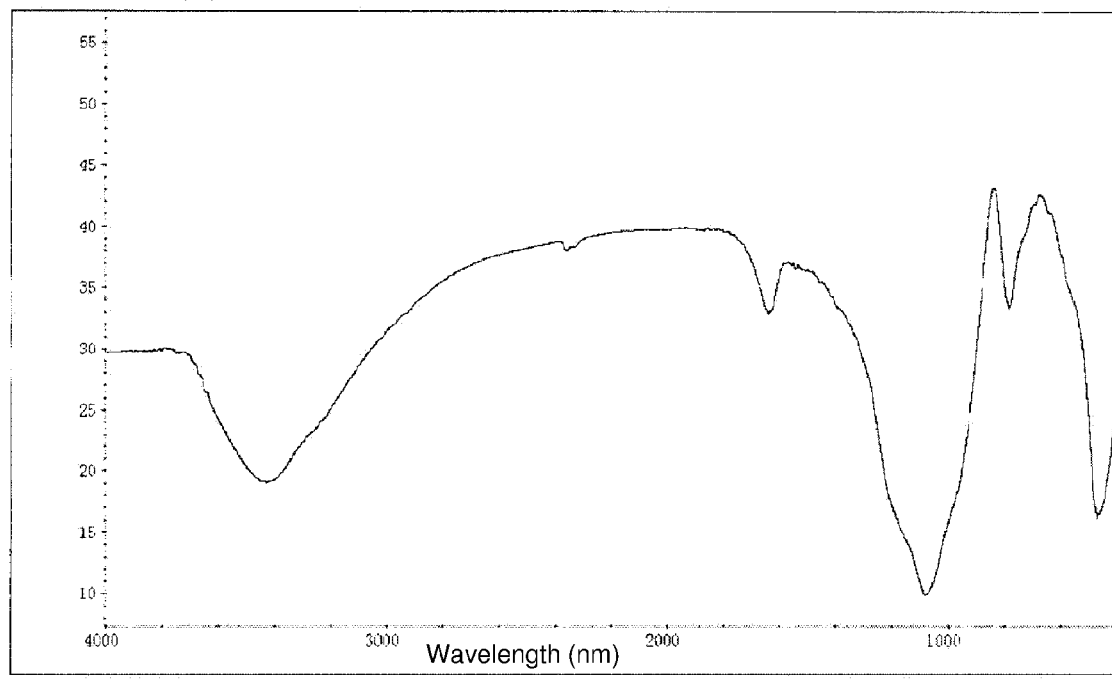
FIG. 4 is an infrared chart of a surface-modified silicon dioxide prepared according to Example 1.

As shown in FIG. 4, silicon dioxide is wrapped by organic groups.

In addition, a BET specific surface area is 100 m²/g.

Oil absorption test: di-n-butyl phthalate is dropped into 100 g of silicon dioxide while stirring until silicon dioxide is agglomerated into a mass in the form of loose particles, a volume of di-n-butyl phthalate consumed is calculated, and a liphophilic value of silicon dioxide obtained by Example 1 is 1.5 mL/g A water surface contact angle is 135°.

EXAMPLE 2

1. 10 kg of rice hulls are collected and treated by industrial flue gas so as to remove metal ions, impurities, and dusts, which is specifically conducted as follows:

As shown in FIG. 7, a reaction tank 15 is configured. The reaction tank has a height of 15 m, an inner volume of 1000 m³. A gas distributor 9 provided with microporous aerators is arranged at a lower part of the reaction tank, a circulating liquid outlet 8 is disposed on a wall of the reaction tank beneath the gas distributor, and a gas outlet 12 is disposed at a top of the reaction tank. A bottom of the reaction tank is a tapered part 11 used to collect precipitants and is provided with a precipitant outlet 10. An upper part of the reaction tank is provided with a mist eliminator 14 and a grid-like package pressing plate 13. The mist eliminator 14 is arranged above the grid-like package pressing plate 13.

When using the reaction tank, rice hulls 5 and water are firstly added to the reaction tank. The rice hulls 5 tend to float on the water surface. The grid-like package pressing plate is used to press the rice hulls packages down below the water surface and is then fixed. The gas outlet is maintained at a closed state, and the industrial flue gas is ejected out of the microporous aerators of the gas distributor. Because of the closed reaction tank and the microporous aeration condition, the pressure of the industrial flue gas in the reaction tank sharply increases, and the amount of carbon dioxide of the industrial flue gas dissolved in water reaches 20 times of that in the normal temperature and the normal pressure, and the solubility is 4 g of carbon dioxide dissolving in 100 g of water. Produced carbonic acid solution reacts with the rice hulls floating thereon to form precipitant. After the reaction, the rice hulls are washed and desalinated water is used to wash and squeeze the rice hulls so as to remove attached metal ions from the rice hulls. 80% of metal ions are removed, and the reaction tank is capable of treating 100 tons rice hulls once.

During the treating process (after the treatment), the pressure in the reaction tank can be regulated during the treating process (or the reaction tank is ventilated after the treatment) by controlling the open degree of the gas outlet arranged on the reaction tank. Carbonic acid solution residue after the treatment is introduced out of the reaction tank via the circulating liquid outlet and can be reused as a nutrient solution for plants.

2. 1 kg of the rice hulls treated by the industrial flue gas are collected and added to a hydrochloric acid solution having a molar concentration of 0.05 M, and a resulting mixture is immersed in an ice bath at a temperature of 10° C. for 6 h. Surplus solutions and the hydrochloric acid solution are leached, a filtrate is removed and a composite containing an organic matter and silicon is obtained and dried.

3. The composite containing the organic matter and silicon is placed within nitrogen atmosphere and heated to a temperature of 350° C. at a heating rate of 20° C./min, after heat preservation for 2 h, a fine $SiO_2$ powder sample is obtained. It is known from tests that the $SiO_2$ powder is in an amorphous structure, has a grain size of 80 nm, a BET specific surface area of 120 m²/g, an oil absorption value of 2.5 mL/g, and a water surface contact angle of 130°.

EXAMPLE 3

1. 10 kg of rice hulls are collected and treated by industrial flue gas in order to remove metal ions, impurities, and dusts, which is specifically conducted as follows:

(1) As shown in FIGS. 5-6, a water storage reactor 1 having a depth of 7 m and both a width and a length of 100 m is constructed. 25 gas dispersion apparatus for discharging industrial flue gas are disposed at a bottom part of the water storage reactor. Each gas dispersion apparatus comprises a longitudinal gas pipe 2 and at least one annular gas pipe 3 being horizontally arranged and communicating with an upper end of the longitudinal gas pipe.

Specifically, a plurality of gas jetting holes (not shown in the drawings) is circumferentially disposed on the annular gas pipe and faces inclinedly downwards, so that a vortex agitation of the water body is produced by the ejected flue gas. An angle between an axis of the gas jetting hole and a horizontal plane is 20°. A projection of the axis of the gas jetting mouth on the horizontal plane is tangent to an annular edge of the annular gas pipe 3, and the gas jetting holes are disposed on the annular gas pipe 3 in a clockwise direction or a counter clockwise direction.

Specifically, a plurality of gas jetting mouths is disposed on a pipe wall of the longitudinal gas pipe 2 and faces inclinedly upwards. An angle between an axis of each gas jetting mouth and a vertical direction is 20°.

Specifically, the gas jetting hole or gas jetting mouth of the gas dispersion apparatus is provided with a plurality of microporous aerators, and the industrial flue gas is ejected out of the microporous aerators.

Specifically, a distance between a height of the annular gas pipe 3 and the bottom of the pool is 2 m.

As shown in FIGS. 7-8, the annular gas pipe 3 comprises: an upper layer annular gas pipe 3.1, a middle layer annular gas pipe 3.2, and a lower layer annular gas pipe 3.3. The upper layer annular gas pipe 3.1, the middle layer annular gas pipe 3.2, and the lower layer annular gas pipe 3.3 have sequentially increased diameters and are arranged on the longitudinal gas pipe 2 from top to bottom to form a tower configuration.

As shown in FIG. 8, the longitudinal gas pipe 2 is disposed at a center of the annular gas pipe 3 and communicates with the annular gas pipe 3 via a transvers gas pipe 6.

A bore diameter of the gas jetting hole is 0.01 mm, and a bore diameter of the gas jetting mouth is between 4 and 6 mm.

(2) The rice hulls 5 are packed and the rice hulls packages are threw into the water storage reactor 1, and then a package pressing strip 7 is used to press the rice hulls packages downward below a water surface.

(3) The industrial flue gas containing carbon dioxide discharged from biomass power plant is treated by a dust collecting equipment for removing dust therefrom, introduced to a gas main 4, and ejected into the water storage reactor containing water having a depth of 5 m by the gas dispersion apparatus 2. Under the action of the pressure, the solubility of carbon dioxide of the industrial flue gas is 1 g of carbon dioxide dissolved in 100 g of water. Carbonic acid solution produced acidifies the rice hulls 5 and reacts with metal ions to produce a precipitant. After the reaction, the rice hulls 5 are washed and desalinated water is used to wash and squeeze the rice hulls so as to remove the attached metal ions from the rice hulls 5.

In the process of rice hulls treatment, soluble matters and precipitants are produced. The soluble matters are abundant in nitrogen, phosphorus, potassium, sodium, and small organic molecules. The precipitants are primarily metal carbonates or oxides containing aluminum, calcium, magnesium, iron, and manganese. Reaction insoluble matters and the dust in the flue gas are precipitated in the bottom of the water storage reactor to form a sediment layer. A cycle for the treatment of the rice hulls using the water storage reactor is 2 days. After being washed twice, the rice hulls is further washed and squeezed by deionized water, so that between 60% and 75% of metal ions of the rice hulls are removed. The water storage reactor is capable of treating 2500 tons rice hulls once.

2. 1 kg of the rice hulls after the pretreatment by the industrial flue gas in Example 1 are collected and added to 20 L of an acetic acid solution having a molar concentration of 0.5 M. A resulting mixture is placed in an ice bath at a temperature of 5° C. for 8 hrs. After that, surplus solution and the acetic acid solution are leached to remove a filtrate and to obtain a composite containing an organic matter and silicon. The composite containing the organic matter and silicon is washed by deionized water for three times, air dried, and grinded, and then dried at a temperature of 110° C.

3. The composite containing the organic matter and silicon is placed in a tube furnace in the presence of nitrogen and is heated to a temperature to 450° C. After heat preservation for 1 h, a fine $SiO_2$ powder sample is obtained. It is known from tests that $SiO_2$ powder is in an amorphous structure, has a grain size of 100 nm, a BET specific surface area of 80 m²/g, an oil absorption value of 2.0, and a water surface contact angle of 128°.

EXAMPLE 4

1 Kg of the rice hulls after the pretreatment by the industrial flue gas in Example 1 are collected and added to 5 L of a phosphoric acid solution having a molar concentration of 0.05 M. A resulting mixture is placed in an ice bath at a temperature of 5° C. for reaction for 8 hrs. After that, surplus solution and the phosphoric acid solution are leached to remove a filtrate and to obtain a composite containing an organic matter and silicon. The composite containing the organic matter and silicon is washed by deionized water for three times, air dried, and grinded, and then dried at a temperature of 110° C.

The composite containing the organic matter and silicon is placed in a tube furnace in the presence of nitrogen and heated to a temperature to 350° C. at a heating rate of 10° C./min, after heat preservation for 2 h, a $SiO_2$ powder sample is obtained. It is known from tests that $SiO_2$ powder has a grain size of 60 nm, a BET specific surface area of 120 m²/g, an oil absorption value of 2.0, and a water surface contact angle of 138°.

EXAMPLE 5

1 kg of the rice hulls after the pretreatment by the industrial flue gas in Example 1 are collected and added to 5 L of a phosphoric acid solution having a molar concentration of 0.05 M. A resulting mixture is placed in an ice bath at a temperature of 5° C. for reaction for 5 h. After that, surplus solution and the phosphoric acid solution are leached to remove a filtrate and to obtain a composite containing an organic matter and silicon. The composite containing the organic matter and silicon is washed by deionized water for three times, air dried, and grinded, and then dried at a temperature of 110° C.

The composite containing the organic matter and silicon is placed in a tube furnace in the presence of nitrogen and heated to a temperature to 500° C. at a heating rate of 10° C./min, after heat preservation for 2 h, a $SiO_2$ powder sample is obtained. It is known from tests that $SiO_2$ powder has a grain size of 250 nm, a BET specific surface area of 60 $m^2/g$, an oil absorption value of 1.0, and a water surface contact angle of 10°, which indicates that the hydrophobic property of $SiO_2$ is not good.

Methods for testing the liphophilic value in Examples 2-5 are the same as that in Example 1. In addition, to achieve a better removal effect of metal ions, the two methods (by using the water storage reactor and using the reaction tank) for treating the industrial flue gas can be combined, that is, a primary crude treatment is performed in the water storage reactor, and a secondary fine treatment is performed in the reaction tank, and the subsequent steps are successively carried out.

The invention claimed is:

1. A method for preparing surface-modified nano silicon dioxide from rice hulls, the method comprising:
   1) pretreating rice hulls using a treating gas containing $CO_2$ to remove metal ions, impurities, and dusts, and desiccating and grinding the rice hulls;
   2) submerging the rice hulls into a dilute solution of a solute selected from the group consisting of phosphoric acid, boric acid, hydrochloric acid, formic acid, acetic acid, propionic acid, butyric acid, or a strong-acid-weak-base salt for between 4 and 8 hrs, controlling an immersion temperature not to exceed 10° C., leaching a resulting mixture, removing a filtrate, and desiccating the rice hulls; and
   3) calcining the rice hulls in the absence of oxygen at a temperature of between 300 and 450° C., whereby obtaining a surface-modified nano silicon dioxide.

2. The method of claim 1, wherein the treating gas containing $CO_2$ in step 1) is industrial flue gas.

3. The method of claim 2, wherein the pretreating of the rice hulls using the treating gas containing $CO_2$ in step 1) comprises:
   i) providing a water storage reactor, disposing a gas dispersion device at a bottom of the water storage reactor, and filling the water storage reactor with water;
   ii) bagging the rice hulls and placing them in the water storage reactor, and submerging them in the water;
   iii) allowing industrial flue gas to be bubbled into the water via the gas dispersion device to increase a solubility of carbon dioxide of the industrial flue gas in the water to produce a carbonic acid solution;
   iv) allowing the carbonic acid solution to react with metal ions in the rice hulls to yield a precipitate; and
   v) washing the rice hulls collected in step iv) to remove the precipitate, and squeezing the rich hulls, whereby removing the metal ions from the rice hulls.

4. The method of claim 3, wherein the gas dispersion apparatus is provided with gas jetting holes configured to horizontally or vertically agitate water to form vortexes; and the industrial flue gas is ejected from the gas jetting holes.

5. The method of claim 3, wherein
   the gas dispersion apparatus comprises a longitudinal gas pipe and at least one annular gas pipe horizontally arranged and communicating with an upper end of the longitudinal gas pipe; and
   a plurality of gas jetting holes is circumferentially disposed on the annular gas pipe and faces inclinedly downwards so that the ejected flue gas enables the water to produce a transverse vortex agitation.

6. The method of claim 5, wherein a plurality of gas jetting mouths is disposed on a pipe wall of the longitudinal gas pipe and faces inclinedly upwards.

7. The method of claim 2, wherein the pretreating of the rice hulls using the treating gas containing $CO_2$ in step 1) comprises:
   a) arranging a gas distributor provided with microporous aerators in a lower part of a reaction tank, arranging a circulating fluid outlet on a wall of the reaction tank beneath the gas distributor, arranging a gas outlet at a top of the reaction tank, arranging a precipitant outlet at a bottom part of the reaction tank, and arranging a movable grid-like package pressing plate in the upper part of the reaction tank;
   b) filling the reaction tank with rice hulls and water, pressing the rice hulls below a water surface using the grid-like package pressing plate, fixing the grid-like package pressing plate, and controlling the gas outlet at a close state;
   c) ejecting the industrial flue gas from the microporous aerator of the gas distributor, utilizing a pressure of the industrial flue gas in the reaction tank to increase a solubility of carbon dioxide of the industrial flue gas in the water and to produce a carbonic acid solution, and allowing the carbonic acid solution to react with metal ions of the rice hulls to produce a precipitant; and
   d) washing the rice hulls after the reaction, and using desalinated water to wash and squeeze the rice hulls to remove attached metal ions from the rice hulls.

8. The method of claim 2, wherein an immersion temperature in step 2) is between −5 and 5° C.; and a ratio of a weight of the rice hulls to a volume of the dilute solution for immersion is 1: 5-20 g/mL.

9. The method of claim 2, wherein step 2) further comprises washing and grinding before desiccating.

10. The method of claim 2, wherein a heating rate in step 3) is between 8 and 20° C./min; and a time for calcination in the absence of oxygen is between 1 and 3 hrs.

11. The method of claim 4, wherein an angle between an axis of each gas jetting hole and a horizontal plane is between 5 and 35°, and an angle between an axis of each gas jetting mouth and a vertical direction is between 10 and 45°.

12. The method of claim 4, wherein a pore diameter of the gas jetting hole is between 0.005 and 0.012 mm, and a pore diameter of the gas jetting mouth is between 4 and 6 mm.

* * * * *